ated with light having a wave-
United States Patent
Braun et al.

[11] Patent Number: 5,919,341
[45] Date of Patent: Jul. 6, 1999

[54] DIFLUOROCHLORACETYL, DICHLORACETYL AND TRICHLORACETYL CHLORIDE PREPARATION

[75] Inventors: Max Braun, Wedemark; Werner Rudolph, Hannover; Kerstin Eichholz, Langenhagen, all of Germany

[73] Assignee: Solvay Fluor und Derivate GmbH, Hannover, Germany

[21] Appl. No.: 08/981,423

[22] PCT Filed: Jun. 17, 1997

[86] PCT No.: PCT/EP96/02596

§ 371 Date: Dec. 23, 1997

§ 102(e) Date: Dec. 23, 1997

[87] PCT Pub. No.: WO97/00847

PCT Pub. Date: Jan. 9, 1997

[30] Foreign Application Priority Data

Jun. 23, 1995 [DE] Germany ............................ 195 22 533
May 17, 1996 [DE] Germany ............................ 196 20 018

[51] Int. Cl.$^6$ ............................ C07C 51/00; C07C 51/58
[52] U.S. Cl. .................. 204/157.87; 204/157.89; 562/840; 562/860; 562/861
[58] Field of Search ................. 204/157.87, 157.89; 562/840, 860, 861

[56] References Cited

U.S. PATENT DOCUMENTS 2,736,695  2/1956  Calfee et al. ......................... 204/158

FOREIGN PATENT DOCUMENTS 1069137  1/1958  Germany.
2118540  1/1972  Germany.

*Primary Examiner*—Kathryn Gorgos
*Assistant Examiner*—Edna Wong
*Attorney, Agent, or Firm*—Evenson, McKeown, Edwards & Lenahan, P.L.L.C.

[57] ABSTRACT

A process for preparing chlorodifluoroacetyl chloride from 1,1-difluoro-2,2-dichloroethylene and dichloroacetyl chloride from trichloroethylene or 1,1,2,2-tetrachloroethane, in which the starting compounds are continuously reacted in the gaseous phase with oxygen to obtain a photochemical oxidation reaction, chlorine being added as a sensitizer, the reaction mixture being irradiated with light having a wavelength $\lambda \geq 280$ nm, the reaction preferably being carried out unpressurized. Particularly high yields with height selectivity are achieved by using doped high pressure mercury vapor lamps to irradiate the reaction mixture.

18 Claims, No Drawings

5,919,341

DIFLUOROCHLORACETYL, DICHLORACETYL AND TRICHLORACETYL CHLORIDE PREPARATION

This is a national stage application of PCT/EP96/02596 filed Jun. 17, 1997.

FIELD OF INVENTION

The invention relates to a method for the production of chlorodifluoro-, dichloro- and trichloroacetyl chloride by photochemical oxidation.

BACKGROUND INFORMATION AND PRIOR ART

Dichloro- and trichloroacetyl chloride are intermediates in chemical synthesis. For example, the herbicides, which are described in the International Application WO 93/24483 dated Dec. 9, 1993 (Chemical Abstracts 120, 1994, Reference 245064y) and which are particular pyrrolidone compounds, can be synthesized using dichloroacetyl chloride. Trichloroacetyl chloride can be used to synthesize trifluoroacetyl chloride, which represents, in turn, a pharmaceutical and agrochemical intermediate. This is disclosed in the French Patent Application 2,592,376 dated Jul. 3, 1987 (Chemical Abstracts 108, 1988, Reference 94077d).

The synthesis of di- or trichloroacetyl chloride by photochemical oxidation of trichloroethylene or tetrachloroethylene with oxygen in the presence of chlorine while irradiating with short-wave light in the liquid phase, is known from the German Patent 759 963. The oxidation of tetrachloroethylene through quartz glass in the presence of chlorine while irradiating with light having a wavelength of 436 nm (=436 m$\mu$) with formation of $CCl_3C(O)Cl$ is described by Schott and Schumacher in Z. Phys. Chem. 49 (1941), pages 107 to 125 and the corresponding oxidation of trichloroethylene is described in Z. Phys. Chem. Section B, 37 (1937), pages 365 to 373. However, according to that patent, the photooxidation in the gas phase can be carried out only on a very small scale because of the high evolution of heat and the difficulty of dissipating the heat from the gaseous products; consequently, the experts turned to liquid phase oxidation (already for the method of the German patent 759 963). As disclosed in the European patent EP-B-O 422 520, however, epoxides are formed to a greater extent by liquid phase oxidation. According to the European patent, the starting material is passed in a thin film through the reaction zone. A further improvement in the liquid phase method is the objective of the European patent application EP-A-O 623 578 dated Nov. 9, 1994. For that method, in which trichloroethylene is reacted with oxygen in the liquid phase in the absence of chlorine with irradiation with short-wave light, certain nitrogen-containing bases (secondary amines) are added, in order to accelerate the conversion of epoxides, which are produced as a by-product, into dichloroacetyl chloride. The addition of such a catalyst, which of course must be removed once again from the reaction mixture or product, greatly complicates the method.

Chlorodifluoroacetyl chloride is also an intermediate in chemical synthesis, for example, for the production of dyes. It is possible to trifluoromethylate alkyl and aryl halides by means of a derivative of chlorodifluoroacetyl chloride, namely by the methyl ester, in the presence of potassium fluoride and copper iodide. The aforementioned methyl ester is also an intermediate for the synthesis of difluorocarbene (G. A. Wheaton and D. J. Donald in J. Fluorine Chem. 8 (1976), pages 97 to 100). Difluorocarbene is used for the production of insecticides (EP-A 198 791 (U.S. Pat. No. 4,701,563)). The production of trifluorocarbene from trifluoromethyl phenyl mercury and other compounds of this type is a problem from environmental points of view.

The German Offenlegungsschrift 43 42 601 A1 discloses the production of, among other compounds, chlorodifluorodiacetyl chloride by the photochemical oxidation of 1,1-difluoro-1,2,2-trichloroethane under activating irradiation in the gas phase without the addition of sensitizers. The German Offenlegungsschrift 44 20 763 A1 discloses a corresponding method with the addition of elementary chlorine as sensitizer and irradiation with light having a wavelength $\lambda \geq 290$ nm. The German Auslegeschrift 1 069 173 discloses, among other things, the production of chlorodifluorodiacetyl chloride from 1,1-difluoro-2,2-dichloroethylene or from 1,1-difluoro-1,2,2-trichloroethane or 1,1-difluoro-2,2,2-trichloroethane by photochemical oxidation. If the starting material is a saturated ethane derivative, the reaction for this embodiment should advisably be carried out in the presence of chlorine.

OBJECT OF THE INVENTION

It is an object of the present invention to provide a method for the synthesis of chlorodifluoro-, dichloro- and trichloroacetyl chloride by a photochemical oxidation, with which the desired products can be produced technically easily and selectively, particularly with respect to the suppression of epoxide formation and in an acceptable yield. This objective is accomplished by the method of the present invention.

SUMMARY OF THE INVENTION

Pursuant to the invention, the carboxylic acid chlorides, which have the formula CClXYC(O)Cl and are substituted in the $\alpha$ position by at least one chlorine atom and in which X represents H or F and Y represents Cl or F, are produced by a photochemical oxidation of $CCl_2=CHCl$ or $CHCl_2CHCl_2$ if X=H and Y=Cl, or of $CCl_2=CCl_2$ if X and Y represent Cl, or of $CF_2=CCl_2$ if X represents F and Y represents F as C2 reactant, with oxygen as reactant in the gas phase, the C2 reactants being introduced into the reactor in vapor form and the method being carried out continuously.

Preferably, the reaction is carried out in the presence of elementary chlorine with exposure to activating radiation with light having a wavelength of $\lambda \geq 280$ nm. Here also, the reactants are reacted in the gas phase.

For the irradiation, irradiating lamps, such as Philips fluorescent tubes, are used, which only irradiate UV light having a wavelength at or above 280 nm ($\lambda \geq 280$ nm). Irradiation through quartz glass is possible here. The only prerequisite for this variation is that these lamps emit in the wavelength region, in which elementary chlorine absorbs. Alternatively, irradiation lamps, such as medium or high pressure mercury vapor radiators are used, which also emit a few lines in the region below 280 nm ($\lambda < 280$ nm). For this variation, it is necessary to irradiate through a glass, which is transparent only for light of a wavelength of 280 nm or longer ($\lambda \geq 290$ nm) and thus filters out the shorter wavelength portion of the irradiation having a wavelength of $\lambda < 280$ nm. Borosilicate glasses are, for example, very suitable for this purpose. Such glasses usually contain 7 to 13% of $B_2O_3$, 70 to 80% $SiO_2$, 2 to 7% $Al_2O_3$ and 4 to 8% $Na_2O+K_2O$, as well as 0 to 5% alkaline earth metal oxides. The known trademarks for borosilicate glasses are DURAN, PYREX and SOLIDEX. Of course, the reaction can also be carried out by using, on the one hand, an irradiating lamp, which emits light above the given wavelength, and additionally glasses, which are transparent for light above the given wavelength (that is, which are correspondingly opaque to light below the given wavelength).

Also very suitable for the irradiation are lamps, such as high pressure mercury vapor lamps which, because of a doping agent, emit predominantly or exclusively in the wavelength region at or above 280 nm. High pressure mercury vapor radiators, for example, have quite intensive bands in the region of 254 nm which, as described above, are filtered out, for example, by borosilicate glass. This line is heavily suppressed by high pressure mercury vapor radiators, doped with metal iodides. The frequently superproportional increase in the conversion rate achieved with radiators, so doped, is surprising. Outstanding results with respect to the conversion rate and the selectivity are attained with high pressure mercury vapor radiators, which are doped with gallium iodide, and particularly with radiators, which are doped with thallium iodide or cadmium iodide. Such radiators are also used advantageously in conjunction with a glass, which filters out the shorter wavelength portion of the radiation having a $\lambda<280$ nm. It is advisable and technically advantageous to utilize the whole of the range of radiations having wavelengths above the limits named.

With respect to the temperature and pressure, the reaction can be carried out so that there is no condensation within the photoreactor. Preferably, the reaction is carried out at temperatures up to 200° C. The production of dichloro- and chlorodifluoroacetyl chloride is carried out particularly at a temperature ranging from 50° to 150° C. and the production of trichloroacetyl chloride at a temperature ranging from 100° to 200° C. It is also possible to work at a reduced pressure; preferably however, the pressure is at least 1 bar absolute, particularly 1 to 10 atmospheres (absolute) and particularly 1 to 3 atmospheres (absolute). In particular, however, the reaction is carried out "unpressurized". Within the scope of the invention, the expression "unpressurized" means that, aside from the atmospheric pressure (that is, about 1 atmosphere), the delivery pressure of the oxygen gas (or of the oxygen-containing gas; for example, air can be used) and of the chlorine and the pressure of the hydrogen chloride gas, which may be formed by the reaction, there is no additional pressure on the reaction mixture. The total pressure in the reactor advisably then is less than 2 bar absolute or even lower than 1.5 bar absolute depending on the delivery pressure, but more than atmospheric pressure.

In relation to the reaction temperature and pressure, it has proven to be particularly advantageous to work so that the C2 starting compound is in the gaseous (or vapor) state in the reactor. However, the reaction product is condensed. The formation of phosgene is suppressed hereby and the selectivity is increased. The production of dichloroacetyl chloride from trichloroethylene is carried out, for example, at a temperature between 80° and 110° C., the pressure then being between 1 and 2 bar absolute, for example.

Advantageously, for this variation, the reaction product is drawn off in liquid form from the bottom of the irradiation equipment, while the gaseous starting compounds (oxygen, chlorine, C2 reactants) are supplied separately or as a mixture further above in the direction of the head of the irradiation equipment or at the head itself.

The method is carried out advantageously in a flow-through apparatus, starting material (the appropriate starting compound containing hydrogen and halogen, chlorine and oxygen) being supplied to the flow-through apparatus continuously and reaction product, corresponding to the amount supplied, being drawn off also continuously.

The molar ratio of C2 reactant to elementary chlorine can vary within a wide range, for example, from 1:0.01 to 1:1. Particularly good results are achieved if the molar ratio of the starting compound to the elementary chlorine falls within the range of 1:0.08 to 1:0.2.

The molar ratio of C2 reactants to oxygen can also vary within a wide range. Advisably, at least 0.3 moles are used per mole of starting compound. Particularly good results are achieved if the molar ratio of the starting compound to the oxygen falls with the range of 1:0.3 to 1:5, preferably 1:0.4 to 1:5, especially 1:0.4 to 1:1.18 and particularly 1:0.5 to 1:1.8. Very good results are already obtained if the molar ratio of starting compound to oxygen is between 1:0.5 and 1:1.1. The oxygen can be used in the form of air or as a mixture of oxygen and an inert gas; preferably, however, pure oxygen is used.

The activating irradiation preferably is carried out with radiators, which emit light, which lies at least partially within the UV range. For example, high pressure and medium pressure mercury vapor radiators are suitable. Fluorescent tubes, such as Philips fluorescent tubes with selective emission at 350 nm, can also be used. The material used for the corresponding components of the apparatus advisably are transparent to UV. As already stated, quartz can be used, provided that the radiator emits light at or above a wavelength of 280 nm. Otherwise or alternatively, the aforementioned borosilicate glasses are used.

With regard to the purity of the product, it is desirable that as little water as possible be present during the reaction. If necessary, the reactants can be freed from entrained water by known methods, for example, by means of a molecular sieve.

The average residence time in the reaction vessel preferably is between 0.01 and 30 minutes, particularly between 0.01 and 3 minutes and especially between 0.5 and 3.0 minutes. Good results are already achieved at very short residence times, such as those between 0.04 and 0.5 minutes. The optimum average residence time, which depends on such factors as the lamp output and the geometric parameters of the irradiation equipment (flow-through apparatus), can be determined by simple small-scale tests and analysis of the product stream, for example, by gas chromatography.

Better conversion rates and higher selectivity can be achieved if, instead of a single irradiating lamp with a particular output, two or more lamps of lower output but the same total output are used in reactors connected in series. Moreover, the product advisably is isolated upon leaving the respective reactions, for example, by freezing. Good swirling of the reaction mixture, for example, by suitable baffles, frequently also is of advantage.

The method offers some surprising advantages. The high conversion rate and the high selectivity despite the preferred use of elementary chlorine is also surprising (if any, only traces of chlorinated by-products are found), especially if high pressure mercury vapor radiators, doped with metal iodide, are used. The inventive method has advantages, such as the following: it is technically simple; it is selective and only slight amounts of epoxides and phosgene are formed; no catalyst is required; it can be carried out continuously and also unpressurized, if so desired; the quantum yield is very high; the reaction rate is very high.

The following examples are intended to explain the invention further without limiting its extent. The safety precautions, required for working with molecular oxygen, are observed.

EXAMPLE 1
Continuous Production of Dichloroacetyl Chloride (DCAC) from 1,1,2,2-Tetrachloroethane (TCE) Through Borosilicate Glass and by Chlorine Sensitization Into a 400 mL Pyrex glass photoreactor with a cadmium iodide-doped high pressure mercury vapor radiator (available as the TQ 718 Z 3 of Firma Heraeus Noblelight), a mixture of 1,1,2,2-tetrachloroethane (from a pre-vaporizer at a temperature of 200° C.), oxygen and chlorine were supplied in gaseous form from below in a molar ratio of 1:1.1:0.1 and irradiated at a wavelength of more than 280 nm through Pyrex glass with a lamp output of 700 W at a temperature within the reactor of 170° C. The dosage was 2 moles per hour. The gaseous product stream, leaving the reactor, contained DCAC in a selectivity of 79%, the conversion being 83%.

EXAMPLE 2
Continuous Production of Dichloroacetyl Chloride (DCAC) by the Photooxidation of Trichloroethylene Through Borosilicate Glass and by Means of Chlorine Sensitization in the Gas Phase at 90° C.

$$CCl_2=CHCl + 1/2\ O_2 \xrightarrow{h\nu} CHCl_2C(O)Cl$$

Into a 400 mL photolysis immersion shaft Pyrex glass reactor (with a double jacket for the heating), equipped with a high pressure mercury vapor radiator, which is not doped (available as the TQ 718 of Firma Heraeus Noblelight), a mixture of trichloroethylene (from the pre-vaporizer with a temperature of 150° C.), oxygen and chlorine were supplied in gaseous form in the molar ratio of 1:1.1:0.1 and irradiated through Pyrex glass (borosilicate glass) at a wavelength longer than 280 nm with a lamp of 700 W output, the internal temperature of the reactor being 90° C. The educts are supplied continuously from above to the reactor and discharged at the lower outlet of the reactor into a methanol/dry ice trap. The dosage was 3.3 moles of trichloroethylene per hour. The GC analysis of the condensation products revealed dichloroacetyl chloride in a selectivity of 91%. Furthermore, 2% trichloroethylene epoxide was formed. The conversion of the trichloroethylene was 83%. Surprisingly, chlorination products of trichloroethylene or of DCAC were not found. The product was purified further by distillation.

EXAMPLE 3
Continuous Production of Dichloroacetyl Chloride (DCAC) by the Photooxidation of Trichloroethylene Through Borosilicate Glass and by Means of Chlorine Sensitization in the Gas Phase at 90° C. with a Lower Lamp Output The procedure was the same as that for Example 2. However, the lamp output was 500 W, whereas the dosage was the same. The selectivities were 92% for DCAC and 2% for trichloroethylene epoxide. The conversion of trichloroethylene was of the order of 69%.

EXAMPLE 4
Continuous Production of Dichloroacetyl Chloride (DCAC) by the Photooxidation of Trichloroethylene Through Borosilicate Glass and by Means of Chlorine Sensitization in the Gas Phase at 90° C. at a Higher Dosage The procedure was the same as that for Example 2. However, the lamp output was 500 W, the ratio of trichloroethylene to oxygen to chlorine was 1:1.1:0.06 and the trichloroethylene dosage was 3.52 moles per hour. The selectivities were 96% for DCAC and 1.6% for trichloroethylene epoxide. The conversion of trichloroethylene was 42%.

EXAMPLE 5
Continuous Production of Dichloroacetyl Chloride (DCAC) by Photooxidation of Trichloroethylene Through Pyrex Glass and by Means of Chlorine Sensitization in the Gas Phase at 90° C. Using a Doped Radiator The procedure was the same as that for Example 4. However, it was carried out with a thallium iodide-doped mercury radiator (available as the TQ 718 Z 2 from Firma Heraeus Noblelight). The selectivities corresponded to those of Example 4; however, the conversion was 64%.

EXAMPLE 6
Continuous Production of Trichloroacetyl Chloride by the Photooxidation of Tetrachloroethylene by Means of Irradiation Through Pyrex Glass and Sensitizing with Chlorine in the Gas Phase at 150° C.

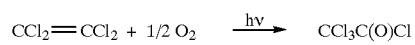

$$CCl_2=CCl_2 + 1/2\ O_2 \xrightarrow{h\nu} CCl_3C(O)Cl$$

Into a 400 mL photolysis immersion shaft glass reactor (double jacketed on the outside for heating), equipped with a high pressure mercury vapor radiator, which was not doped (available as the TQ 718 from Firma Heraeus Noblelight), a mixture of tetrachloroethylene (from a pre-vaporizer at a temperature of 170° C.), oxygen and chlorine was supplied in gaseous form in the molar ratio of 1:1.1:0.1 and irradiated through Pyrex glass (borosilicate glass) at a wavelength longer than 280 nm with a lamp of 500 W output at an internal reactor temperature of 150° C. The educts were supplied continuously from above to the reactor and the products discharged at the lower outlet of the reactor into a methanol/dry ice trap. The dosage was 2.7 moles of tetrachloroethylene per hour. GC analysis of the condensation products revealed trichloroacetyl chloride in a selectivity of 96%. The conversion was 56%. (The percentages are given in each case as GC area %.)

Comparable results were obtained when the reaction was carried out in equipment made from DURAN 50® glass.

EXAMPLE 7
Continuous Production of DCAC by Photooxidation of Trichloroethylene by Irradiation Through Quartz Glass Without Chlorine in the Gas Phase at 90° C.

Into a 400 mL Pyrex glass photoreactor with a not doped high pressure mercury vapor radiator (available as the TQ 718 of Firma Heraeus Noblelight), a mixture of trichloroethylene (from a pre-vaporizer at a temperature of 150° C.) and oxygen was supplied in gaseous form in a molar ratio of 1:1.1 and irradiated through quartz glass with a lamp output of 500 W at a temperature within the reactor of 90° C. The educts were supplied continuously here to the reactor from above and the products were discharged at the lower outlet of the reactor into a methanol/dry ice trap. The dosage was 2.2 moles of trichloroethylene per hour. GC analysis of the condensation products revealed dichloroacetyl chloride in a selectivity of 83%. Furthermore, 3.5% trichloroethylene epoxide, 11% phosgene and 2.8% oxalyl dichloride were formed. The conversion of the trichloroethylene was 63%.

EXAMPLE 8
Continuous Production of DCAC by Photooxidation of Trichloroethylene by Irradiation Through Quartz Glass Without Chlorine in the Gas Phase at 150° C.

Into a 400 mL Pyrex glass photoreactor with a not doped high pressure mercury vapor radiator (available as the TQ 718 of Firma Heraeus Noblelight), a mixture of trichloroethylene (from a pre-vaporizer at a temperature of 150° C.) and oxygen was supplied from below in gaseous form in a molar ratio of 1:1.1 and irradiated through quartz glass with a lamp output of 700 W at a temperature within the reactor of 150° C. The dosage was 2.2 moles of trichloroethylene per hour. The gaseous product stream leaving the reactor at the top contained DCAC in a selectivity of 67.4%. Furthermore, trichloroethylene epoxide (5.7%), phosgene (17.2%), tetrachloroethylene (1.0%), pentachloroethyne (1.9%), hexachloroethane (0.3%), oxalyl dichloride (2.6%) and trichloroacetyl chloride (3.1%) were formed as byproducts. The conversion of the trichloroethylene was 48.3%.

EXAMPLES 9 AND 10
Production of Chlorodifluoroacetyl Chloride With Fluorescent Lamps as a Source of UV Light
In General A Duran 50® photoreactor with a capacity of 4.3 L was used. The irradiation was conducted with a TLK4010R UV lamp. This is a conventional, commercial Philips UV fluorescent lamp with a nominal output of 40 watt and equipped with a reflecting layer to increase the radiation output. Oxygen, chlorine and 1,1-dichloro-2,2-difluoroethylene (1112a) were mixed and then passed in a gaseous form into the reactor.
Analysis The conversion is determined by the complete hydrolysis of the gas taken off from the reactor, whereupon the chlorodifluoroacetic acid content is determined with the help of an ion chromatograph. The selectivity was determined gas chromatographically (gas sample after reactor, before hydrolysis).

EXAMPLE 9
Production of Chlorodifluoroacetyl Chloride (CDFAC)
Starting mixture: 0.6 moles of 1112a, 1.0 mole of oxygen and 0.11 moles of chlorine.
Duration of trial: 20 minutes 1112a is evaporated and, mixed with the other components of the reaction, passed through the reactor. After the reactor, there is a wash bottle for hydrolyzing the chlorodifluoroacetyl chloride formed. The reactor temperature was 85° to 91° C. and the irradiation was carried out with two 40 watt lamps. The conversion was 99.58% and the selectivity, based on the CDFAC formed, was 90.8%.

EXAMPLE 10
Starting mixture: 0.57 moles of 1112a, 0.61 moles of oxygen and 0.04 moles of chlorine
Duration of trial: 20 minutes The procedure was identical with that of Example 9, with the exception that the irradiation was carried out with only one 40 watt fluorescent lamp. The conversion was 95.4% and the selectivity, based on the CDFAC formed, was 90.26%.

We claim:

1. A method for producing a carboxylic acid chloride substituted in the α position by at least one chlorine atom and corresponding to the formula CClXYC(O)Cl wherein X represents H or F, and Y represents Cl or F, said method comprising introducing a C2 reactant in vapor form into a reactor and photochemically oxidizing the C2 reactant in the gas phase with oxygen in the gas phase in the presence of elemental chlorine by exposing the gas phase mixture to activating irradiation with light having a wavelength $\lambda \geq 280$ nm, the method being carried out continuously, and the C2 reactant being selected from:

a) $CCl_2$=CHCl or $CHCl_2CHCl_2$ if X represents H and Y represents Cl, or b) $CCl_2$=$CF_2$, if X represents F and Y represents F.

2. A method according to claim 1, wherein X represents H, and the C2 reactant is $CCl_2$=CHCl.

3. A method according to claim 1, wherein the photochemical oxidation is carried out unpressurized.

4. A method according to claim 1, wherein the C2 reactant and the elemental chlorine are present in a molar ratio of C2 reactant to elemental chlorine of 1:0.01 to 1:1.

5. A method according to claim 4, wherein the C2 reactant and the elemental chlorine are present in a molar ratio of C2 reactant to elemental chlorine of 1:0.08 to 1:0.2.

6. A method according to claim 1, wherein the C2 reactant and the oxygen are present in a molar ratio of C2 reactant to oxygen of 1:0.3 to 1:5.

7. A method according to claim 6, wherein the C2 reactant and the oxygen are present in a molar ratio of C2 reactant to oxygen of 1:0.4 to 1:1.8.

8. A method according to claim 1, wherein the photochemical oxidation is carried out at a temperature of up to 200° C.

9. A method according to claim 8, wherein the photochemical oxidation is carried out at a temperature ranging from 50° to 150° C.

10. A method according to claim 1, wherein the photochemical oxidation is carried out at a temperature which lies between the boiling point of the C2 reactant and the boiling point of the carboxylic acid chloride reaction product.

11. A method according to claim 10, wherein the produced carboxylic acid chloride is drawn off in the liquid state from the reactor bottom.

12. A method according to claim 1, wherein an average residence time in the reactor between 0.01 and 30 minutes.

13. A method according to claim 12, wherein the average residence time in the reactor is between 0.5 minutes and 3.0 minutes.

14. A method according to claim 1, wherein the activating irradiation is emitted by a doped radiator.

15. A method according to claim 14, wherein said doped radiator is a high pressure mercury vapor lamp doped with a metal iodide.

16. A method according to claim 15, wherein said metal iodide comprises gallium iodide, potassium iodide or cadmium iodide.

17. A method according to claim 1, wherein said photochemical oxidation is carried out in the absence of a basic catalyst which accelerates the rearrangement of intermediate products.

18. A method acccording to claim 1, wherein said photochemical oxidation is carried out in the absence of a basic catalyst which accelerates the rearrangement of epoxides.

* * * * *